US008399661B2

(12) United States Patent
Sheu et al.

(10) Patent No.: US 8,399,661 B2
(45) Date of Patent: Mar. 19, 2013

(54) SULFUR-CONTAINING COMPOUND, METHOD OF PREPARATION AND PHARMACEUTICAL USES THEREOF

(75) Inventors: Jyh-Horng Sheu, Kaohsiung (TW); Chih-Hua Chao, Kaohsiung (TW); Zhi-Hong Wen, Kaohsiung (TW)

(73) Assignee: National Sun Yat-Sen University, Kaohsiung (TW)

( * ) Notice: Subject to any disclaimer, the term of this patent is extended or adjusted under 35 U.S.C. 154(b) by 566 days.

(21) Appl. No.: 12/172,633

(22) Filed: Jul. 14, 2008

(65) Prior Publication Data
US 2009/0062285 A1 Mar. 5, 2009

(30) Foreign Application Priority Data

Aug. 30, 2007 (TW) ................. 96132313 A

(51) Int. Cl.
C07D 265/30 (2006.01)
C07C 321/04 (2006.01)
C07C 309/04 (2006.01)
C07C 317/04 (2006.01)

(52) U.S. Cl. ............... 544/158; 560/9; 562/123; 568/31; 568/37

(58) Field of Classification Search .................. 544/158; 560/9; 562/123; 568/31, 37
See application file for complete search history.

(56) References Cited

U.S. PATENT DOCUMENTS

| | | | |
|---|---|---|---|
| 2,416,052 | A | 2/1947 | Gribbins |
| 3,517,013 | A | 6/1970 | Akamatsu |
| 3,888,912 | A | 6/1975 | Burguette |
| 4,093,591 | A | 6/1978 | Kline |
| 4,356,010 | A | 10/1982 | Meyer zu Riemsloh |
| 4,656,308 | A | 4/1987 | Schirmann et al. |
| 4,778,869 | A | 10/1988 | Schirmann et al. |
| 5,026,807 | A | 6/1991 | Ohira et al. |
| 5,214,116 | A | 5/1993 | Matsuoka et al. |
| 5,457,172 | A | 10/1995 | Curci et al. |
| 5,587,499 | A | 12/1996 | Curci et al. |
| 5,959,147 | A | 9/1999 | Wakao et al. |
| 7,229,987 | B2 | 6/2007 | Ammenn et al. |
| 7,254,072 | B2 | 8/2007 | Kuroda |
| 7,417,911 | B2 | 8/2008 | Kuroda |
| 7,595,292 | B2 | 9/2009 | Brocchini et al. |
| 7,939,630 | B2 | 5/2011 | Brocchini et al. |
| 2010/0033954 | A1 | 2/2010 | Boonekamp et al. |

FOREIGN PATENT DOCUMENTS

| | | |
|---|---|---|
| BE | 666830 | 3/1965 |
| CA | 2484233 A1 | 11/2003 |
| EP | 0020000 B1 | 12/1980 |
| EP | 0367577 A1 | 5/1990 |
| EP | 0382477 A1 | 8/1990 |
| EP | 0463947 A1 | 1/1992 |
| EP | 0558370 A1 | 9/1993 |
| FR | 2071386 | 12/1969 |
| GB | 877402 | 4/1960 |
| GB | 1123672 | 7/1965 |
| JP | 41007066 | 4/1946 |
| JP | 45035292 | 11/1970 |
| JP | 51001733 | 1/1976 |
| JP | 5359636 | 5/1978 |
| JP | 53085420 | 7/1978 |
| JP | 62149666 | 7/1987 |
| JP | 01094346 A | 4/1989 |
| JP | 01099039 A | 4/1989 |
| JP | 01102461 A | 4/1989 |
| JP | 01236252 | 9/1989 |
| JP | 4221329 | 8/1992 |
| JP | 06080624 | 3/1994 |
| JP | 07300451 | 11/1995 |
| JP | 07300452 | 11/1995 |
| JP | 08-283234 | 10/1996 |
| JP | 2002121182 A | 4/2002 |
| JP | 2005529923 A | 6/2005 |
| JP | 2007527382 | 9/2007 |
| JP | 350270 | 8/2008 |
| JP | 2008195689 | 8/2008 |
| JP | 2010506371 | 2/2010 |
| NL | 299516 | 8/1965 |
| NL | 6503759 | 9/1965 |
| WO | 9622238 A1 | 7/1996 |
| WO | 03097047 A1 | 11/2003 |
| WO | 2005002994 A1 | 1/2005 |
| WO | 2005007197 A2 | 1/2005 |
| WO | 2008044170 A2 | 4/2008 |

OTHER PUBLICATIONS

Cerf, et al. Document No. 116:152603 retrieved from CAPLUS; Jan. 1, 1992.*
EP Search Report, App. No. 08015281.2 (Nov. 24, 2009).
Freeman F., et al., Preparation of 1,3-diketones and their reaction with bis (trialkyltin) or bis(triphenyltin) sulfide-boron trichloride; J. of Organic Chem., vol. 57, pp. 1722-1727, XP002555056 (1992).
Ueda I., et al., Synthesis and Pharmacological Properties of N-[3-{3-(1-Piperidinylmethyl)phenoxy}propyl]-2-(2-hydroxyethylthio)acetamide and Related Compounds as Antiulcer Agents, Chemical and Pharmaceutical Bulletin, vol. 38, pp. 3035-3041, XP002555584 (1990).
Niyazymbetov M.E., et al., Electrocatalytic Addition of Thiols to Activated Olefins, Russian Chemical Bulletin, vol. 40 pp. 240-241 (1991).
Office Action, ROC (Taiwan) Pat. App. No. 096132313 (Mar. 4, 2010).
Peter Libby, Inflammation and cardiovascular disease mechanisms, Am J Clin Nutr. 83(suppl):456S-60S (2006).
Russell Ross, Ph.D., Atherosclerosis—An Inflammatory Disease, Mechanisms of Disease, 340(2):115-126 (Jan. 14, 1999).

(Continued)

Primary Examiner — Shawquia Young
(74) Attorney, Agent, or Firm — Husch Blackwell LLP; Robert C. Haldman; H. Frederick Rusche

(57) ABSTRACT

The invention relates to a sulfur-containing compound and the preparation thereof. The invention also relates to the uses of the sulfur-containing compound in inhibiting inducible nitric oxide synthase and/or cyclooxygenase-2 and in treating the diseases associated with inducible nitric oxide synthase and/or cyclooxygenase-2. This invention also describes a series of chemical analogues of the said sulfur-containing compound and the preparation of these compounds.

16 Claims, 5 Drawing Sheets

OTHER PUBLICATIONS

Lucas, et al., Atherosclerosis: role of chemokines and macrophages, Cambridge Univ. ISSN 1462-3994, pp. 1-18 (Nov. 5, 2001).

Slamon Gordon, The macrophage, BioEssays, 17(11):977-986 (1995).

F. Cipollone, COX-2 and prostaglandins in atherosclerosis, Lupus, 14:756-759 (2005).

J.J. Boyle, Macrophage Activation in Atherosclerosis: Pathogenesis and Pharmacology of Plaque Rupture, Current Vascular Pharmacology 3:63-68 (2005).

Osiecki, et al., The Role of Chronic Inflammation in Cardiovascular Disease and its Regulation by Nutrients, Alternative Medicine Review, 9(1):32-53 (2004).

Baker, et al., Cycloox genase-2 is Widely Expressed in Atherosclerotic Lesions Affecting Native and Transplanted Human Coronary Arteries and Colocalizes With Inducible Nitric Oxide Synthase and Nitrotyrosine Particularly in Macrophages, Arterioscler Thromb Vase Biol., pp. 646-655 (1999).

Buttery, et al., Inducible Nitric Oxide Synthase is Present within Human Atherosclerotic Lesions and Promotes the Formation and Activity of Peroxynitrite, Laboratory Investigation, 75(1):77-85 (1996).

Burleigh, et al., Cyclooxygenase-2 Promotes Early Athrosclerotic Lesion Formation in LDL Receptor-Deficient Mice, http://www.circulationaha.org (Apr. 27, 2008).

Hayashi, et al., Selective iNOS inhibitor, ONO1714 successfully retards the development of high-cholesterol diet induced atherosclerosis by novel mechanism, Atherosclerosis 187:316-324 (2006).

Turini, et al., Cyclooxygenase-2:A Therapeutic Target, Annu. Rev. 53:35-57 (2002).

Handy, et al., A comparison of the effects of L-NAME, 7-NI and L-NIL on carrageenan-induced hindpaw oedema and NOS activity, British J of Pharmacology, 123:1119-1126 (1998).

Osborne, et al., Effects of intrathecal administration of nitric oxide synthase inhibitors on carrageenan-induced thermal hyperalgesia, British J of Pharmacology, 126:1840-1846 (1999).

Moalem, et al., Immune and inflammatory mechanisms in neuropathic pain, Science Direct, Brain Research Reviews, 51:240-264 (2006).

Cuzzocrea, et al., Effects of Combination M40403 and Dexamethasone Therapy on Joint Disease in a Rat Model of Collagen-Induced Arthritis, Arthritis & Rheumatism, 52:6, pp. 1929-1940 (Jun. 2005).

Misko, et al., Mediation of inflammation by encephalitogenic cells: interferon γ induction of nitric oxide synthase and cyclooxygenase 2, J. of Neuroimmunology, 61:195-204 (1995).

Toriyabe, et al., Contribution of Interaction between Nitric Oxide and Cyclooxygenases to the Production of Prostaglandins in Carrageenan-induced Inflammation, Anesthesiology, 101(4):983-990 (Oct. 2004).

Lopez-Vales, et al., Effects of COX-2 and iNOS Inhibitors Alone or in Combination With Olfactory Ensheathing Cell Grafts After Spinal Cord Injury, SPINE, 31(10):1100-1106 (2006).

Wen, et al., D-2-Amino-5-phosphonopentanoic acid inhibits intrathecal pertussis toxin-induced thermal hyperalgesia and protein kinase Cγ up-regulation, Brain Research, 963:1-7 (2003).

Bennett, et al., A peripheral mononeuropathy in rat that produces disorders of pain sensation like those seen in man, Pain, 33:87-107 (1988).

Hargreaves, et al., A new and sensitive method for measuring thermal nociception in cutaneous hyperalgesia, Pain, 32:77-88 (1988).

Berger, et al., Zinc reduces intimal hyperplasia in the rat carotid injury model, Atherosclerosis, 175:229-234 (2004).

Chen, et al., Magnolol induces apoptosis in vascular smooth muscle, Naunyn-Schmiedeberg's Arch Pharmacol., 368:127-133 (2003).

Boullerne, et al., Anti-S-Nitrosocysteine Antibodies Are a Predictive Marker for Demyelination in Experimental Autoimmune Encephalomyelitis: Implications for Multiple Sclerosis, The J. of Neuroscience, 22(1):123-132 (Jan. 1, 2002).

Liu, et al., Bilirubin as a potent antioxidant suppresses experimental autoimmune encephalomyelitis: implications for the role of oxidative stress in the development of multiple sclerosis, J. of Neuoimmunology, 139:27-35 (2003).

\* cited by examiner

SULFUR-CONTAINING COMPOUND, METHOD OF PREPARATION AND PHARMACEUTICAL USES THEREOF

BACKGROUND OF THE INVENTION

1. Field of the Invention

The invention relates to a novel sulfur-containing compound. Said sulfur-containing compound has ability to inhibit the function of inducible nitric oxide synthase (iNOS) and/or cyclooxygenase-2 (COX-2).

2. Description of the Related Art

With the progression of civilization, we human beings not only have longevity, but also emphasize the quality of our daily lives. However, a specific and effective drug is still absent for many diseases nowadays, such as cancer, chronic pain and atherosclerosis.

Inflammation has been proven to play an important role in the occurrence of several diseases in many studies. The occurrence of the inflammation-related diseases is highly associated with chronic and long-term inflammation induced by free radicals, pollution, food, ages, and pressure.

Atherosclerosis leads to remold a blood vessel and further causes the reduction of the inside diameter of the vessel. Therefore, it is an important risk factor of one of the leading causes of death, acute and lethal cardiovascular diseases, such as myocardial infarction, stroke and peripheral vascular diseases (Libby, Am J Clin Nutr 83:456 S-460S, 2006). Atherosclerosis is proven to be a chronic inflammatory cardiovascular disease (Ross, N Engl J Med 340: 115-126, 1999). When intima cells of the blood vessel are pressed or injured, monocytes are induced to differentiate into macrophages and accumulate abundantly around the injured tissue. Through a series of inflammatory reactions, smooth muscle cells of the blood vessel proliferate and inflammatory cells accumulate, and such reactions damage the blood flow and lead to cardiovascular diseases finally (Lucas and Greaves, Exp Rev Mol Med 3:1-18, 2001; Gordon, Bioessays 17:977-986, 1995). In animal model studies, the inflammatory critical factors of inducible nitric oxide synthase and cyclooxygenase-2 are shown to play an important role in atherosclerosis (Cipollone, Lupus 14:756-759, 2005; Boyle, Curr Vasc Pharmacol 3:63-68, 2005). Furthermore, bulk of inducible nitric oxide synthase and cyclooxygenase-2 is expressed in the human atherosclerosis tissue that comprises macrophages and proliferated smooth muscle cells (Baker et al, Arterioscler Thromb Vasc Biol 19:646-655, 1999; Buttery et al, Lab Invest 75:77-85, 1996). Presently, inducible nitric oxide synthase and cyclooxygenase-2 inhibitors are proven to significantly prevent the occurrence of atherosclerosis (Burleigh et al, Circulation 105:1816-23, 2002; Hayashi et al, Atherosclerosis 187:316-324, 2006; Osiecki, Altern Med Rev. 9: 32-53, 2004).

According to the definition made by International Association for the Study of Pain (IASP), pain is an unpleasant sensory and emotional experience associated with actual or potential tissue damage, or described in terms of such damage. With the extension of longevity, the opportunities and duration of pain are raised. To estimate in the conservative way, the global anodyne consumption reaches around one hundred billion US dollars. Improving life quality through pain control is an important subject. Among various pains, the factors of neuropathic pain are diverse, such as reduced distal circulation due to diabetes mellitus, neuron damage due to amputation or injury, viral infection and unknown reasons. Clinically, anodynes are divided into addictive anodynes and non-addictive anodynes. The addictive anodyne mainly comprises opiate, but the effect thereof to neuropathic pain is not satisfactory. The non-addictive anodyne comprises a steroid type and a non-steroid type. The steroid anodyne relives pain mainly through an anti-inflammatory pathway. However, the steroid anodyne is nonspecific, and the side effects are significant. The long-term usage is prohibited. On the other hand, the non-steroid anodyne comprises a pain-relieving type (such as Panadol) and an anti-inflammatory type (such as Aspirin). A non-steroid anti-inflammatory drug (NSAID) is now known to be safe with fewer side effects. The mechanism of a specific NSAID is through inhibiting inducible nitric oxide synthase and cyclooxygenase-2 pathways to relieve pain (Turini and DuBois, Annual Rev Med 53:35, 2002; Handy et al, Br J Pharmacol 123:1119-1126, 1998; Osborne et al, Br J Pharmacol 126:1840-1846, 1999). The product of NO or PGE2 catalyzed by inducible nitric oxide synthase or cyclooxygenase-2 is shown to be critical to the occurrence, maintenance and sensitivity of pain in the central neural system and periphery tissues (Moalem and Tracey, Brain Res Rev 51:240-264, 2006). Compared to using nerve blockers for pain relieving, administering inducible nitric oxide synthase and cyclooxygenase-2 inhibitors does not affect movement and neuron. Therefore, it is an important aspect for drug development.

SUMMARY OF THE INVENTION

One object of the invention is to provide a novel sulfur-containing compound. Said sulfur-containing compound can be chemically synthesized and can significantly inhibit the functions of inflammatory proteins in vitro. Furthermore, the sulfur-containing compound is shown to be able to treat a disease associated with inducible nitric oxide synthase and/or cyclooxygenase-2.

Another object of the invention is to provide a method for preparing the sulfur-containing compound mentioned above.

Still another object of the invention is to provide a method for inhibiting inducible nitric oxide synthase and/or cyclooxygenase-2.

Yet still another object of the invention is to provide a method for treating a disease associated with inducible nitric oxide synthase and/or cyclooxygenase-2 comprising administering a subject with said sulfur-containing compound.

DETAILED DESCRIPTION OF THE INVENTION

Figure 1:
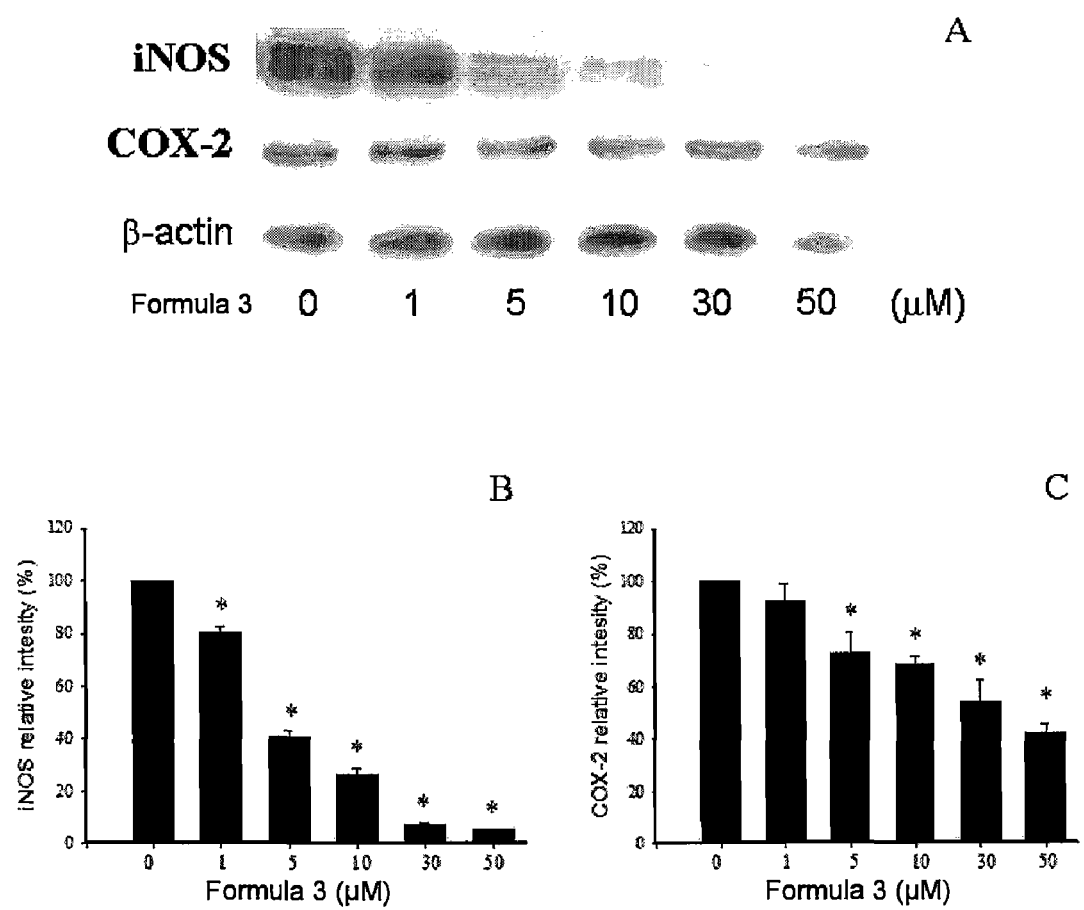
FIG. 1 shows the effect of the compound represented by formula 3 at different concentrations on inducible nitric oxide synthase and cyclooxygenase-2 expressed by macrophages stimulated by lipopolysaccharide (LPS). A: results of Western blot; B: the statistical data of the effect of the compound represented by formula 3 at different concentrations on the expression of inducible nitric oxide synthase; C: the statistical data of the effect of the compound represented by formula 3 at different concentrations on the expression of cyclooxygenase-2. Each test was repeated six times.

The sulfur-containing compound according to the invention is represented by the following general formula 1,

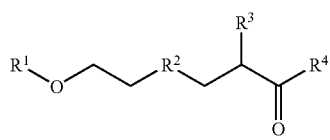

formula 1 wherein:
$R^1$ is selected from the group consisting of H, $R^5$ and $R^5C(=O)$;
$R^2$ is selected from the group consisting of S and $(O=)S(=O)$;
$R^3$ is selected from the group consisting of H, $CH_3$ and $CH_2CH_2C(=O)OR^5$;
$R^4$ is selected from the group consisting of $R^5$, $OR^5$,

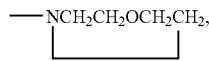

$N(R^5)_2$, $NH_2$, $NHR^5$ and OH; and
$R^5$ is selected from an alkyl group having one to six carbon atoms and an unsubstituted or substituted phenyl group; and preferably, $R^5$ is selected from the group consisting of methyl, ethyl, and unsubstituted phenyl,
provided that when $R^3$ is $CH_2CH_2C(=O)OR^5$, $R^4$ is $OR^5$; and
when $R^1$ is H, $R^1$ is S and $R^3$ is H, $R^1$ is not $CH_3$.

According to the preferred embodiments of the invention, the compound represented by general formula 1 is represented by one of the following formulae 3 to 22,

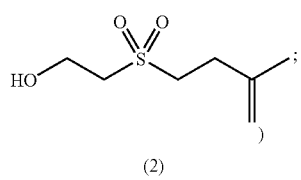

formula 3

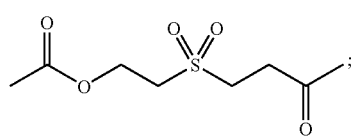

formula 4

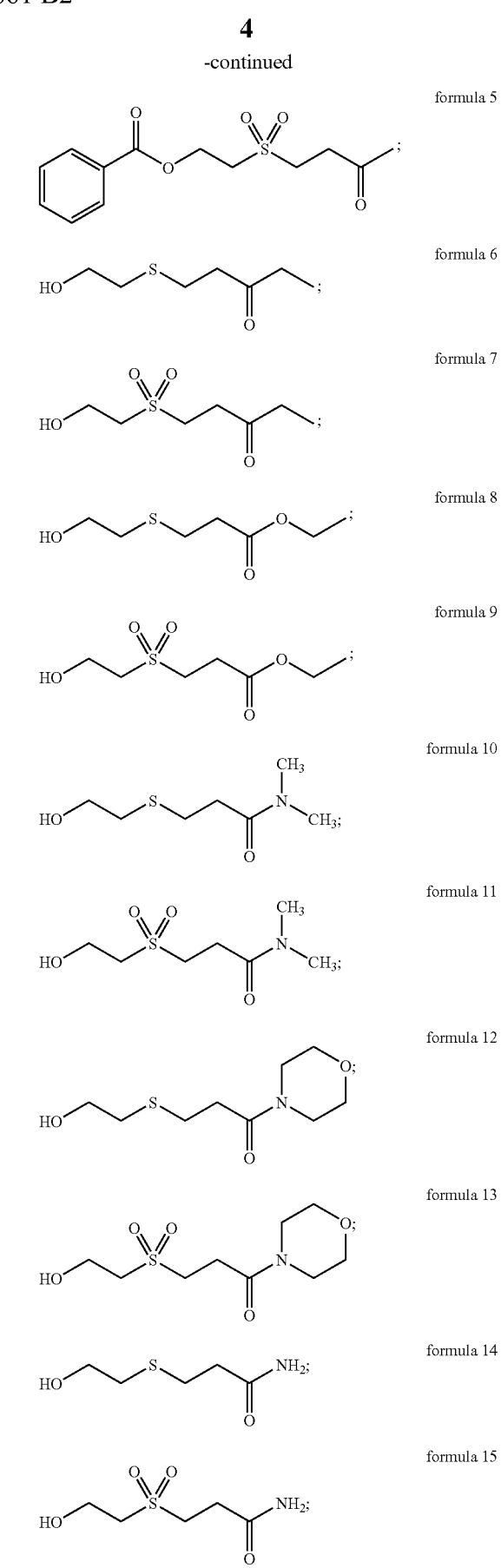

-continued

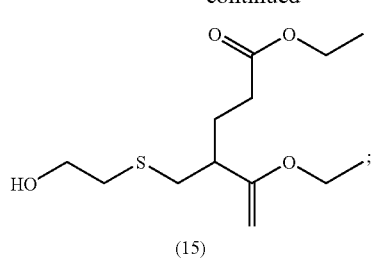
(15)

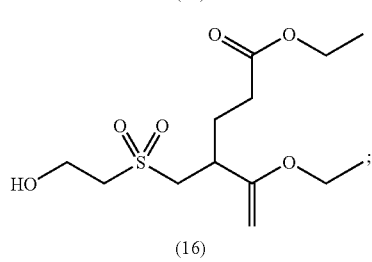
(16)

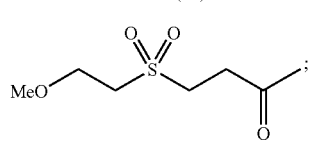
formula 18

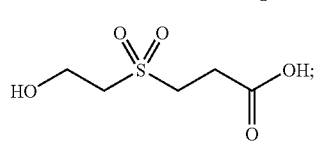
formula 19

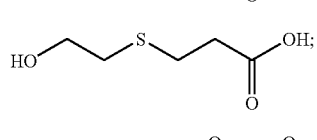
formula 20

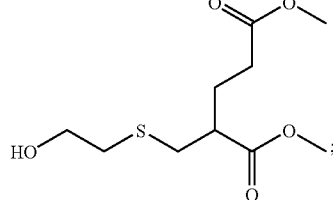
formula 21

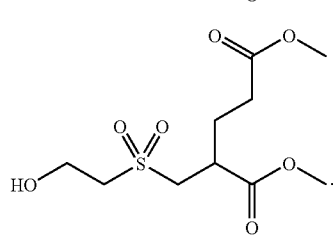
formula 22

The present invention also provides a method for preparing a compound represented by the following general formula 2, formula 2

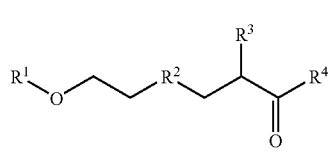

wherein:

$R^1$ is selected from the group consisting of H, $R^5$ and $R^5C(=O)$;

$R^2$ is selected from the group consisting of S and $(O=)S(=O)$;

$R^3$ is selected from the group consisting of H, $CH_3$ and $CH_2CH_2C(=O)OR^5$;

$R^4$ is selected from the group consisting of $R^5$, $OR^5$,

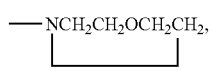

$N(R^5)_2$, $NH_2$, $NHR^5$ and OH; and $R^5$ is selected from an alkyl group having one to six carbon atoms and an unsubstituted or substituted phenyl group;

provided that when $R^3$ is $CH_2CH_2C(=O)OR^5$, $R^4$ is $OR^5$, comprising:

(I) when $R^1$ is H and $R^1$ is S, reacting a compound represented by the following general formula 23, formula 23

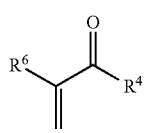

with 2-mercaptoethanol represented by the following formula 24, formula 24

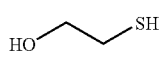

to obtain a compound represented by the following general formula formula 25

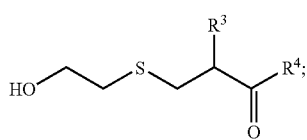

(II) when $R^1$ is $R^5C(=O)$, esterifying the compound represented by general formula 25;
(III) when $R^1$ is $R^5$, alkylating the compound represented by general formula 25;
(IV) when $R^2$ is $(O=)S(=O)$, oxidizing the compound represented by general formula 25;
(V) when $R^1$ is $R^5C(=O)$ and $R^2$ is $(O=)S(=O)$, esterifying and oxidizing the compound represented by general formula 25;
(VI) when $R^1$ is $R^5$ and $R^2$ is $(O=)S(=O)$, alkylating and oxidizing the compound represented by general formula 25; and
(VII) when $R^1$ is H, $R^2$ is S, $R^3$ is H and $R^4$ is $CH_3$, reacting a compound represented by the following formula 27, formula 27

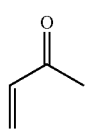

with 2-mercaptoethanol represented by formula 24 in the presence of triethylamine.

Particularly, the method according to the invention is one of the following methods:

(I) When $R^1$ is H and $R^2$ is S, the method of the invention comprises reacting a compound represented by general formula 23

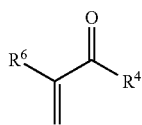

formula 23

(wherein $R^3$ preferably is H)
with 2-mercaptoethanol represented by formula 24 to obtain the compound represented by general formula 25. Preferably, the above reaction is carried out in the presence of triethylamine. In one embodiment of the invention, the reactants are dissolved in acetone and reacted in ice bath. In another aspect, when $R^3$ is $CH_2CH_2C(=O)OR^5$, the reaction is conducted in the absence of a solvent.

(II) When $R^1$ is $R^5C(=O)$, the method according to the invention comprises esterifying the compound represented by general formula 25. Preferably, the above reaction is carried out in the presence of triethylamine. In one embodiment of the invention, the reactants are dissolved in dichloromethane. In one preferred embodiment of the invention, when $R^1$ is $CH_3C(=O)$, the method comprises reacting the compound represented by general formula 25 with acetic anhydride. In one another preferred embodiment of the invention, when $R^1$ is $C_6H_5C(=O)$, the method comprises reacting the compound represented by general formula 25 with benzoyl chloride.

(III) When $R^1$ is $R^5$, the method according to the invention comprises alkylating the compound represented by general formula 25. In one preferred embodiment of the invention, when $R^1$ is $CH_3$, the method comprises reacting the compound represented by general formula 25 with $CH_3I$.

(IV) When $R^2$ is $(O=)S(=O)$, the method according to the invention comprises oxidizing the compound represented by general formula 25. Preferably, the oxidation is carried out with hydrogen peroxide or m-chloroperoxybenzoic acid. In one embodiment of the invention, when using hydrogen peroxide, the oxidation is catalyzed by $MnSO_4 \square H_2O$, and the reactants are dissolved in acetonitrile. When using m-chloroperoxybenzoic acid to carry out the oxidation, the reactants are dissolved in dichloromethane.

(V) When $R^1$ is $R^5C(=O)$ and $R^2$ is $(O=)S(=O)$, the method according to the invention comprises esterifying and oxidizing the compound represented by general formula 25 as mentioned above.

(VI) When $R^1$ is $R^5$ and $R^2$ is $(O=)S(=O)$, the method according to the invention comprises alkylating and oxidizing the compound represented by general formula 25 as mentioned above.

(VII) When $R^1$ is H, $R^2$ is S, $R^3$ is H and $R^4$ is $CH_3$, the method according to the invention comprises reacting a compound represented by formula 27 with 2-mercaptoethanol represented by formula 24 in the presence of triethylamine.

The present invention also provides a method for inhibiting inducible nitric oxide synthase and/or cyclooxygenase-2.

The present invention further relates to a method for treating a disease associated with inducible nitric oxide synthase and/or cyclooxygenase-2 comprising administering a subject with the compound represented by general formula 1. Because the compound represented by general formula 1 has ability to inhibit the accumulation of inducible nitric oxide synthase and/or cyclooxygenase-2, it is useful in treating the diseases associated with inducible nitric oxide synthase and/or cyclooxygenase-2. Many diseases have been reported to be related to the function of inducible nitric oxide synthase and/or cyclooxygenase-2, such as arthritis (Cuzzocrea et al, Arthritis Rheum. 52:1929-40, 2005), multiple sclerosis (Misko et al, J Neuroimmunol. 61:195-204, 1995), inflammatory pain (Toriyabe et al, Anesthesiology 101, 983-990, 2004), and spinal cord injury (Lopez-Vales et al, Spine. 31:1100-6, 2006). Therefore, the disease is preferably selected from the group consisting of inflammation, atherosclerosis, neuropathic pain, inflammatory neointimal proliferation, arthritis, multiple sclerosis, inflammatory pain, and spinal cord injury. In one in vivo model of atherosclerosis in rat, the compound represented by general formula 1 is shown to have the ability to treat atherosclerosis. In another embodiment of the invention, administering the compound represented by general formula 1 through intrathecal injection is effective in treating neuropathic pain. Furthermore, in the multiple sclerosis animal model, the compound represented by general formula 1 is shown to have the ability to treat multiple sclerosis.

The compound represented by general formula 1 can be administered orally or through injection. Preferably, the compound is administered by injection.

The following examples are given for the purpose of illustration only and are not intended to limit the scope of the present invention.

Preparation 1

2-Mercaptoethanol (1.80 g, 98%, 27.14 mmole) and triethylamine (0.53 mL, 3.77 mmole) were added in a round bottom flask containing 22 mL of acetone. Followed by stirring in a 0° C. ice bath, a solution of methyl vinyl ketone (2.31 mL, 27.14 mmole) in 4 mL acetone was dropped into the flask slowly. After the addition, the temperature of the reaction was raised to room temperature, and the reaction was continued for 16 hours. The solvent-free product was subject to silica gel column chromatography to afford a thioether compound represented by the following formula 26 (3.35 g, yield 100%),

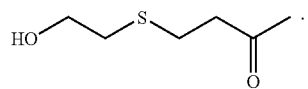

formula 26

Thioether compound represented by formula 26: colorless oil, IR (KBr) $\nu_{max}$ 3405, 1713, 1416, 1362, 1161, 1045, 1010 cm$^{-1}$; $^1$H NMNR (CDCl$_3$, 300 MHz) $\delta_H$ 3.73 (2H, dt, J=5.6, 5.4 Hz), 2.75 (4H, br s), 2.72 (2H, t, J=5.4 Hz), 2.46 (1H, t, J=5.6 Hz, OH) 2.17 (3H, s); $^{13}$C NMR (CDCl$_3$, 75 MHz) $\delta_C$ 207.0 (qC), 60.6 (CH$_2$), 43.7 (CH$_2$), 35.6 (CH$_2$), 30.2 (CH$_3$), 25.4 (CH$_2$); ESIMS m/z 171 [M+Na]$^+$; HRESIMS m/z 171.0458 [M+Na]$^+$ (calculated for C$_6$H$_{12}$O$_2$SNa, 171.0456).

Preparation 2

The thioether compound represented by formula 26 (1.00 g, 6.76 mmole) prepared as Preparation 1 and MnSO$_4\square$H$_2$O (23 mg, 0.14 mmole) were mixed with acetonitrile (156 μL) in a 500 μL round bottom flask (Flask A) and the mixture was stirred vigorously at room temperature. The aqueous solutions of sodium hydrogen carbonate buffer (115 mL, 0.2 M, pH=8.0) and 30% hydrogen peroxide solution (3.38 µL) were charged into a 250 mL flask at 0° C. and stirred well, and then added slowly into Flask A. After reacting for 2 hours, ethyl acetate/isopropyl alcohol (3:1) was added for extraction (200 µL×6). The combined organic extract was concentrated under reduced pressure and the residue was purified over a silica gel column (eluted with hexane/EtOAc=1:3) for obtaining the compound represented by formula 3 (1.03 g, yield 84%).

Compound represented by formula 3: colorless crystals, mp 59-60° C.; IR (KBr) $v_{max}$ 3416, 1715, 1416, 1366, 1311, 1120, 1009 cm$^-$; $^1$H NMR (CDCl$_3$, 300 MHz) $\delta_H$ 4.02 (2H, t, J=5.4 Hz), 3.36 (2H, t, J=7.3 Hz), 3.21 (2H, t, J=5.4 Hz), 2.97 (2H, t, J=7.3 Hz), 2.20 (3H, s); $^{13}$C NMR (CDCl$_3$, 75 MHz) $\delta_C$ 204.9 (qC), 56.0 (CH$_2$), 55.7 (CH$_2$), 48.7 (CH$_2$), 34.9 (CH$_2$), 29.7 (CH$_3$); ESIMS m/z 203 [M+Na]$^+$; HRESIMS m/z 203.0354 [M+Na]$^+$ (calculated for C$_6$H$_{12}$O$_4$SNa, 203.0354).

Preparation 3

To a stirring solution of the thioether compound represented by formula 26 (1.00 g, 6.76 mmole) prepared as Preparation 1 in dichloromethane (64 mL) in a 125 mL round bottom flask was slowly added m-chloroperoxybenzoic acid (2.92 g, 16.90 mmole) in batches. After the addition, the reaction was monitored with TLC until the thioether compound was completely consumed. Then, dichloromethane was removed, and the resulted mixture was added with 100 mL of saturated sodium hydrogen carbonate solution and stirred vigorously. The resulted crude product was extracted with ethyl acetate (100 mL×10) and the combined extract was concentrated under reduced pressure. The obtained product was purified with a silica gel column (eluted with hexane/EtOAc=1:3) to afford the compound represented by formula 3 (1.00 g, yield 82%).

Preparation 4

To a stirring solution of the compound represented by formula 3 (20.0 mg, 0.114 mmole) and triethylamine (25 µL) in dichloromethane (2 mL) was slowly added acetic anhydride (40 µL) at room temperature. The reaction was continued for 16 hours and the solvent-free product was subjected to silica gel column chromatography (eluted with hexane/EtOAc=2:3) for obtaining a compound represented by formula 4 (25.0 mg, yield 98%).

Compound represented by formula 4: colorless oil, IR (KBr) $v_{max}$ 1743, 1720, 1366, 1317, 1234, 1125, 1070, 1036 cm$^{-1}$; $^1$H NMR (CDCl$_3$, 300 MHz) $\delta_H$ 4.52 (2H, t, J=5.8 Hz), 3.36 (2H, t, J=7.2 Hz), 3.34 (2H, t, J=5.8 Hz), 3.03 (2H, t, J=7.2 Hz), 2.25 (3H, s), 2.11 (3H, s); $^{13}$C NMR (CDCl$_3$, 75 MHz) $\delta_C$ 204.0 (qC), 170.2 (qC), 57.5 (CH$_2$), 52.8 (CH$_2$), 48.5 (CH$_2$), 34.9 (CH$_2$), 29.8 (CH$_3$), 20.7 (CH$_3$); ESIMS m/z 245 [M+Na]$^+$; HRESIMS m/z 245.0458 [M+Na]$^+$ (calcd for C$_8$H$_{14}$O$_5$SNa, 245.0460).

Preparation 5

To a stirring solution of the compound represented by formula 3 (20.0 mg, 0.114 mmole) and triethylamine (25 µL) in dichloromethane (2 mL) was slowly added benzoyl chloride (50 µL) at room temperature. The reaction was continued for 5 hours and the solvent-free product was subjected to silica gel column chromatography (eluted with hexane/EtOAc=5:3) for obtaining a compound represented by formula 5 (29.8 mg, yield 92%).

Compound represented by formula 5: colorless crystals, mp=79-80° C.; IR (KBr) $v_{max}$ 1714, 1710, 1315, 1276, 1133, 1119 cm$^{-1}$; $^1$H NMR (CDCl$_3$, 300 MHz) $\delta_H$ 8.04 (2H, d, J=7.5 Hz), 7.60 (1H, t, J=7.5 Hz), 7.47 (2H, t, J=7.5 Hz), 4.78 (2H, t, J=5.7 Hz), 3.48 (2H, t, J=5.7 Hz), 3.41 (2H, t, J=7.2 Hz), 3.03 (2H, t, J=7.2 Hz), 2.21 (3H, s); $^{13}$C NMR (CDCl$_3$, 75 MHz) $\delta_C$ 203.8 (qC), 165.8 (qC), 133.5 (CH), 129.6 (CH× 2), 129.0 (qC), 128.6 (CH×2), 58.0 (CH$_2$), 53.0 (CH$_2$), 48.6 (CH$_2$), 34.9 (CH$_2$), 29.7 (CH$_3$); ESIMS m/z 307 [M+Na]$^+$; HRESIMS m/z 307.0613 [M+Na]$^+$ (calcd for C$_{13}$H$_{16}$O$_5$SNa, 307.0616).

Preparation 6

Similar to Preparation 1, α,β-unsaturated carbonly compounds including ethyl vinyl ketone, ethyl acrylate, N,N-dimethylacrylamide, 4-acryloylmorpholine, and acrylamide were independently reacted with 2-mercaptoethanol to give the corresponding thioether compounds represented by formulas 6 (yield 100%), 8 (yield 100%), 10 (yield 100%), 12 (yield 100%), and 14 (yield 90%), respectively. The above reactions were carried out in the presence of acetone, except for that of preparing the compound represented by formula 14 required the presence of a more polar solvent (methanol/acetone=1:1), due to the unsatisfactory solubility of acrylamide. The intermediates with formulas 6, 8, 10, 12, and 14 were oxidized with hydrogen peroxide, similar to Preparation 2 for obtaining compounds represented by formula 7 (yield 87%), 9 (yield 85%), 11 (yield 87%), 13 (yield 83%), and 15 (yield 84%), respectively. Furthermore, the reaction of ethyl acrylate and 2-mercaptoethanol, proceeded without the presence of a solvent, afforded both compounds represented by formula 8 (yield 45%) and formula 16 (yield 22%). Compound represented by formula 17 was prepared by oxidizing the compound represented by formula 16 with hydrogen peroxide (yield 84%).

Compound represented by formula 6: colorless oil; IR (KBr) $v_{max}$ 3418, 1714, 1458, 1411, 1375, 1361, 1113, 1046, 1013 cm$^{-1}$; $^1$H NMR (CDCl$_3$, 300 MHz) $\delta_H$ 3.75 (2H, t, J=6.2 Hz), 2.70-2.80 (6H, m), 2.48 (2H, q, J=7.3 Hz), 1.06 (3H, t, J=7.3 Hz); $^{13}$C NMR (CDCl$_3$, 75 MHz) $\delta_C$ 209.9 (qC), 60.6 (CH$_2$), 42.0 (CH$_2$), 35.9 (CH$_2$), 34.8 (CH$_2$), 25.3 (CH$_2$), 7.3 (CH$_3$); ESIMS m/z 185 [M+Na]$^+$; HRESIMS m/z 185.0611 [M+Na]$^+$ (calcd for C$_7$H$_{14}$O$_2$SNa, 185.0612).

Compound represented by formula 7: colorless oil; mp=44-45° C.; IR (KBr) $v_{max}$ 3419, 1715, 1312, 1280, 1123 cm$^{-1}$; $^1$H NMR (CDCl$_3$, 300 MHz) $\delta_H$ 4.01 (2H, t, J=5.2 Hz), 3.36 (2H, t, J=7.3 Hz), 3.19 (2H, t, J=5.2 Hz), 2.93 (2H, t, J=7.3 Hz), 2.47 (2H, q, J=7.3 Hz), 1.01 (3H, t, J=7.3 Hz); $^{13}$C NMR (CDCl$_3$, 75 MHz) $\delta_C$ 207.6 (qC), 56.0 (CH$_2$), 55.7 (CH$_2$), 48.8 (CH$_2$), 35.8 (CH$_2$), 33.6 (CH$_2$), 7.5 (CH$_3$); ESIMS m/z 217 [M+Na]$^+$; HRESIMS m/z 217.0508 [M+Na]$^+$ (calcd for C$_7$H$_{14}$O$_4$SNa, 217.0510).

Compound represented by formula 8: colorless oil; IR (KBr) $v_{max}$ 3440, 1732, 1373, 1249, 1185, 1044 cm$^{-1}$; $^1$H NMR (CDCl$_3$, 300 MHz) $\delta_H$ 4.16 (2H, q, J=7.1 Hz), 3.74 (2H, t, J=6.1 Hz), 2.82 (2H, t, J=7.1 Hz), 2.74 (2H, t, J=6.1 Hz), 2.62 (2H, t, J=7.1 Hz), 1.27 (3H, t, J=7.1 Hz); $^{13}$C NMR (CDCl$_3$, 75 MHz) $\delta_C$ 172.1 (qC), 60.8 (CH$_2$×2), 35.1 (CH$_2$), 34.9 (CH$_2$), 26.8 (CH$_2$), 14.2 (CH$_3$); ESIMS m/z 201 [M+Na]$^+$; HRESIMS m/z 201.0563 [M+Na]$^+$ (calcd for C$_7$H$_{14}$O$_3$SNa, 201.0561).

Compound represented by formula 9: colorless oil; IR (KBr) $v_{max}$ 3503, 1732, 1313, 1281, 1120, 1065 cm$^{-1}$; $^1$H NMR (CDCl$_3$, 300 MHz) $\delta_H$ 4.19 (2H, q, J=7.1 Hz), 4.12 (2H, t, J=5.0 Hz), 3.46 (2H, t, J=7.4 Hz), 3.25 (2H, t, J=5.0 Hz), 2.88 (2H, t, J=7.4 Hz), 1.28 (3H, t, J=7.1 Hz); $^{13}$C NMR (CDCl$_3$, 75 MHz) δ$_C$ 170.7 (qC), 61.5 (CH$_2$), 56.2 (CH$_2$), 55.6 (CH$_2$), 49.9 (CH$_2$), 26.8 (CH$_2$), 14.0 (CH$_3$); ESIMS m/z 233 [M+Na]$^+$; HRESIMS m/z 233.0458 [M+Na]$^+$ (calcd for C$_7$H$_{14}$O$_5$SNa, 233.0460).

Compound represented by formula 10: colorless oil; IR (KBr) ν$_{max}$ 3399, 1630, 1500, 1403, 1143, 1048, 1014 cm$^{-1}$; $^1$H NMR (CDCl$_3$, 300 MHz) δ$_H$ 3.77 (2H, t, J=5.9 Hz), 3.02 (3H, s), 2.96 (3H, s), 2.87 (2H, t, J=7.2 Hz), 2.75 (2H, t, J=5.9 Hz), 2.62 (2H, t, J=7.2 Hz); $^{13}$C NMR (CDCl$_3$, 75 MHz) δ$_C$ 171.1 (qC), 60.8 (CH$_2$), 37.0 (CH$_3$), 35.4 (CH$_3$×1, CH$_2$×1), 33.5 (CH$_2$), 26.8 (CH$_2$); ESIMS m/z 200 [M+Na]$^+$; HRESIMS m/z 200.0719 [M+Na]$^+$ (calcd for C$_7$H$_{15}$NO$_2$SNa, 200.0721).

Compound represented by formula 11: colorless oil; IR (KBr) ν$_{max}$ 3371, 1634, 1503, 1405, 1312, 1278, 1119, 1065 cm$^{-1}$; $^1$H NMR (CDCl$_3$, 300 MHz) δ$_H$ 4.06 (2H, t, J=5.2 Hz), 3.49 (2H, t, J=7.2 Hz), 3.25 (2H, t, J=5.2 Hz), 3.03 (3H, s), 2.94 (3H, s), 2.87 (2H, t, J=7.2 Hz); $^{13}$C NMR (CDCl$_3$, 75 MHz) δ$_C$ 169.4 (qC), 56.2 (CH$_2$), 56.0 (CH$_2$), 50.3 (CH$_2$), 37.1 (CH$_3$), 35.7 (CH$_3$), 25.7 (CH$_2$); ESIMS m/z 232 [M+Na]$^+$; HRESIMS m/z 232.0618 [M+Na]$^+$ (calcd for C$_7$H$_{15}$NO$_4$SNa, 232.0619).

Compound represented by formula 12: colorless oil; IR (KBr) ν$_{max}$ 3418, 1633, 1463, 1437, 1271, 1248, 1115, 1067, 1028 cm$^{-1}$; $^1$H NMR (CDCl$_3$, 300 MHz) δ$_H$ 3.76 (2H, t, J=6.0 Hz), 3.69 (4H, m), 3.63 (2H, m), 3.48 (2H, dd, J=4.5, 4.9 Hz), 2.87 (2H, t, J=7.2 Hz), 2.74 (2H, t, J=6.0 Hz), 2.63 (2H, t, J=7.2 Hz); $^{13}$C NMR (CDCl$_3$, 75 MHz) δ$_C$ 169.8 (qC), 66.6 (CH$_2$), 66.3 (CH$_2$), 60.8 (CH$_2$), 45.7 (CH$_2$), 41.9 (CH$_2$), 35.2 (CH$_2$), 33.2 (CH$_2$) 26.8 (CH$_2$); ESIMS m/z 242 [M+Na]$^+$; HRESIMS m/z 242.0815 [M+Na]$^+$ (calcd for C$_9$H$_{17}$NO$_3$SNa, 242.0813).

Compound represented by formula 13: colorless needles; mp=109-110° C.; IR (KBr) ν$_{max}$ 3420, 1637, 1452, 1311, 1275, 1117, 1067, 1028 cm$^{-1}$; $^1$H NMR (CDCl$_3$, 300 MHz) δ$_H$ 4.06 (2H, t, J=5.2 Hz), 3.57-3.67 (6H, m), 3.49 (2H, t, J=7.2 Hz), 3.47 (2H, m), 3.25 (2H, t, J=5.2 Hz), 2.86 (2H, t, J=7.2 Hz); $^{13}$C NMR (CDCl$_3$, 75 MHz) δ$_C$ 168.0 (qC), 66.5 (CH$_2$), 66.3 (CH$_2$), 56.2 (CH$_2$), 56.0 (CH$_2$), 50.2 (CH$_2$), 45.7 (CH$_2$), 42.3 (CH$_2$) 25.3 (CH$_2$); ESIMS m/z 274 [M+Na]$^+$; HRESIMS m/z 274.0722 [M+Na]$^+$ (calcd for C$_9$H$_{17}$NO$_5$SNa, 274.0725).

Compound represented by formula 14: white powder; IR (KBr) ν$_{max}$ 3354, 3196, 1661, 1414 cm$^{-1}$; $^1$H NMR (pyridine-d5, 300 MHz) δ$_H$ 4.02 (2H, t, J=6.7 Hz), 3.13 (2H, t, J=7.2 Hz), 2.93 (2H, t, J=6.7 Hz), 2.82 (2H, t, J=7.2 Hz); $^{13}$C NMR (pyridine-d5, 75 MHz) δ$_C$ 174.3 (qC), 61.7 (CH$_2$), 36.6 (CH$_2$), 35.2 (CH$_2$), 28.1 (CH$_2$); ESIMS m/z 172 [M+Na]$^+$; HRESIMS m/z 172.0407 [M+Na]$^+$ (calcd for C$_5$H$_{11}$NO$_2$SNa, 172.0408).

Compound represented by formula 15: white powder; IR (KBr) ν$_{max}$ 3370, 3200, 1661, 1395 cm$^{-1}$; $^1$H NMR (pyridine-d5, 300 MHz) δ$_H$ 4.35 (2H, t, J=5.6 Hz), 4.06 (2H, t, J=7.6 Hz), 3.64 (2H, t, J=5.6 Hz), 3.25 (2H, t, J=7.6 Hz); $^{13}$C NMR (pyridine-d5, 75 MHz) δ$_C$ 174.3 (qC), 61.7 (CH$_2$), 36.6 (CH$_2$), 35.2 (CH$_2$), 28.1 (CH$_2$); ESIMS m/z 204 [M+Na]$^+$; HRESIMS m/z 204.0305 [M+Na]$^+$ (calcd for C$_5$H$_{11}$NO$_4$SNa, 204.0306).

Compound represented by formula 16: colorless oil; IR (KBr) ν$_{max}$ 3438, 1731, 1377, 1299, 1206, 1162, 1043 cm$^{-1}$; $^1$H NMR (CDCl$_3$, 300 MHz) δ$_H$ 4.10 (2H, q, J=7.0 Hz), 4.05 (2H, q, J=7.0 Hz), 3.65 (2H, t, J=6.0 Hz), 2.54-2.74 (5H, m), 2.28 (2H, m), 1.91 (2H, m), 1.20 (3H, t, J=7.0 Hz), 1.18 (3H, t, J=7.0 Hz); $^{13}$C NMR (CDCl$_3$, 75 MHz) δ$_C$ 174.1 (qC), 172.8 (qC), 60.89 (CH$_2$), 60.86 (CH$_2$), 60.6 (CH$_2$), 45.3 (CH), 35.5 (CH$_2$), 33.6 (CH$_2$), 31.7 (CH$_2$) 26.7 (CH$_2$), 14.22 (CH$_3$), 14.18 (CH$_3$); ESIMS m/z 301 [M+Na]$^+$; HRESIMS m/z 301.1084 [M+Na]$^+$ (calcd for C$_{12}$H$_{22}$O$_5$SNa, 301.1086).

Compound represented by formula 17: colorless oil; IR (KBr) ν$_{max}$ 3439, 1732, 1380, 1312, 1290, 1206, 1120 cm$^{-1}$; $^1$H NMR (CDCl$_3$, 300 MHz) δ$_H$ 4.21 (2H, q, J=7.1 Hz), 4.15 (2H, q, J=7.1 Hz), 4.11 (2H, t, J=5.3 Hz), 3.72 (1H, dd, J=14.2, 9.3 Hz), 3.25 (2H, t, J=5.3 Hz), 3.21 (1H, dd, J=14.2, 4.9 Hz), 3.13 (1H, m), 2.39 (2H, t, J=7.4 Hz), 2.04 (2H, t, J=7.4 Hz), 1.30 (3H, t, J=7.1 Hz), 1.27 (3H, t, J=7.1 Hz); $^{13}$C NMR (CDCl$_3$, 75 MHz) δ$_C$ 173.0 (qC), 172.4 (qC), 61.6 (CH$_2$), 60.8 (CH$_2$), 56.4 (CH$_2$), 55.1 (CH$_2$), 55.8 (CH$_2$), 38.7 (CH), 31.1 (CH$_2$) 27.2 (CH$_2$), 14.1 (CH$_3$), 14.0 (CH$_3$); ESIMS m/z 333 [M+Na]$^+$; HRESIMS m/z 333.0986 [M+Na]$^+$ (calcd for C$_{12}$H$_{22}$O$_7$SNa, 333.0987).

Anti-Inflammation Assay In Vitro

A mouse macrophage cell line, RAW 264.7, purchased from the American Type Culture Collection (ATCC□NO TIB-71) was chosen in the in vitro model. The cells were cultured in DMEM (Dulcbecco/s Modified Eagle medium) containing 10% fetal bovine serum (FBS) and penicillin G (100 U/ml) and streptomycin (100 μg/ml) at 37° C. and 5% CO$_2$. When reaching 80% confluence, the cells were subcultured with trypsin. The cells were subjected to an anti-inflammation assay after subcultured for 36 hours. 3×10$^6$ RAW264.7 cells were cultured in a 10-cm culture dish and administered with lipopolysaccharide (LPS, 0.01 μg/ml; Sigma L2654). After 16 hours, the cells were collected. In an experiment group, the compound represented by formula 3 was added into the culture dish and followed by LPS before 10 minutes.

Assay for Protein Expression of Inducible Nitric Oxide Synthase and/or Cyclooxygenase-2

The collected RAW264.7 cells were dissolved with 200 μL of 4° C. lysis buffer (50 mM Tris [pH 7.5], 150 mM NaCl, 1% TritonX-100, 0.1 mM EDTA, 0.1 mM EGTA, 10 μg PMSF, 1 μg/mL aprotinin, 20 mM NaF, and 0.2 mM Na$_3$VO$_4$). The samples were centrifuged at 25,000 g for 30 minutes at 4° C. for removing the pellet. The supernatant was assayed with Bio-Rad DC protein assay kit (Bio-Rad Laboratories, Hercules, Calif., USA) and the absorbance was read with an ELISA reader (Thermo Electron Corporation, USA) for estimating the protein contents. The calibrated samples with equal volumes were added with a sample buffer (2% SDS, 10% glycerol, 0.1% bromophenol blue, 10% 2-mercaptoethanol, and 50 mM Tris) of the same volume. Proteins were separated with 10% SDS-PAGE and transferred to a PVDF membrane (0.45 mm, Immobilon-P, Millipore, Bedford, Mass., USA) (1.5 A, 4° C., 2.5 hours). The transferred PVDF membranes were blocked with TTBS (Tris-HCl 20 mM, NaCl-137 mM, pH 7.4 and 0.1% Tween 20) containing 5% skim milk at room temperature for 1 hour and reacted with polyclonal anti-inducible nitric oxide synthase antibody (Transduction Laboratories, Lexington, Ky., USA) or polyclonal anti-cyclooxygenase-2 antibody (Cayman, Ann Arbor, Mich., USA) at room temperature for 3 hours. After washed with TTBS three times, the samples were reacted with HRP-conjugated anti-rabbit IgG antibody (1:2000) at room temperature for 1 hour. After washed with TTBS for three times, an enhanced chemiluminescence detection kit was used for reading with the PVDF membrane and exposed with an X-ray film (Kodak X-OMAT LS, Kodak, Rochester, N.Y., USA) for detecting the protein expression. The relative amount was calculated with Image-Pro plus 4.5 software (Media Cybernetics, Silver Spring, USA). The group added with only LPS was taken as 100%. β-actin (monoclonal antibody, Sigma, St Louis, Mo., USA) was taken as an internal control.

The results are shown in FIG. 1. 10 to 30 μM of the compound represented by formula 3 significantly inhibits the effect of inducible nitric oxide synthase of macrophages stimulated by LPS (0.01 μg/ml) and 50% inhibition concentration ($IC_{50}$) is 3.64±0.28 μM. 5 to 30 μM of the compound represented by formula 3 also significantly inhibits the effect of cyclooxygenase-2 of macrophages stimulated by LPS (0.01 μg/ml) and the $IC_{50}$ is 32.1±8.1 μM. However, at a concentration of 50 μM the compound represented by formula 3 inhibits the protein expression of β-actin.

Animal Model

Intrathecal Catheter Operation

The operation was performed according to the description of Wen et al, Brain Res 963:1-7, 2003. The dura mater of male Wistar rats was opened near the foramen magnum and planted with an 8.5-cm PE tube (outer diameter: 0.014 inches, inner diameter: 0.008 inches). The drugs worked near the lumbar, and the end of injection was fixed on the head. Animals those had deficient in motor or blood in the intrathecal catheter were abandoned.

Animal Model of Neuropathic Pain

The model was established similar to the sciatic nerve chronic constriction injury (CCI) established by Bennett and Xie (Pain 33:87-107, 1988). 4-O cat cut line was used to tie four nodes on the sciatic nerve. After one week, the behavior of thermal hyperalgesia was stimulated. The behavior of thermal hyperalgesia was assayed similar to the method established by Hargreaves et al (Pain 32:77-88, 1988) and recorded with an analgesiometer (IITC Inc., Woodland Hills, Calif., USA) for assessing the effect of the compound represented by formula 3 on neuropathic pain relief.

The data of each animal were exhibited with the maximum percent effect (MPE) and analyzed statistically.

MPE (%)=(latency after drug administered−basal latency)/(30 seconds−basal latency)×100%

If a higher MPE was obtained, the effect of pain relief was better, and the maximum value of MPE was 100.

Figure 2:
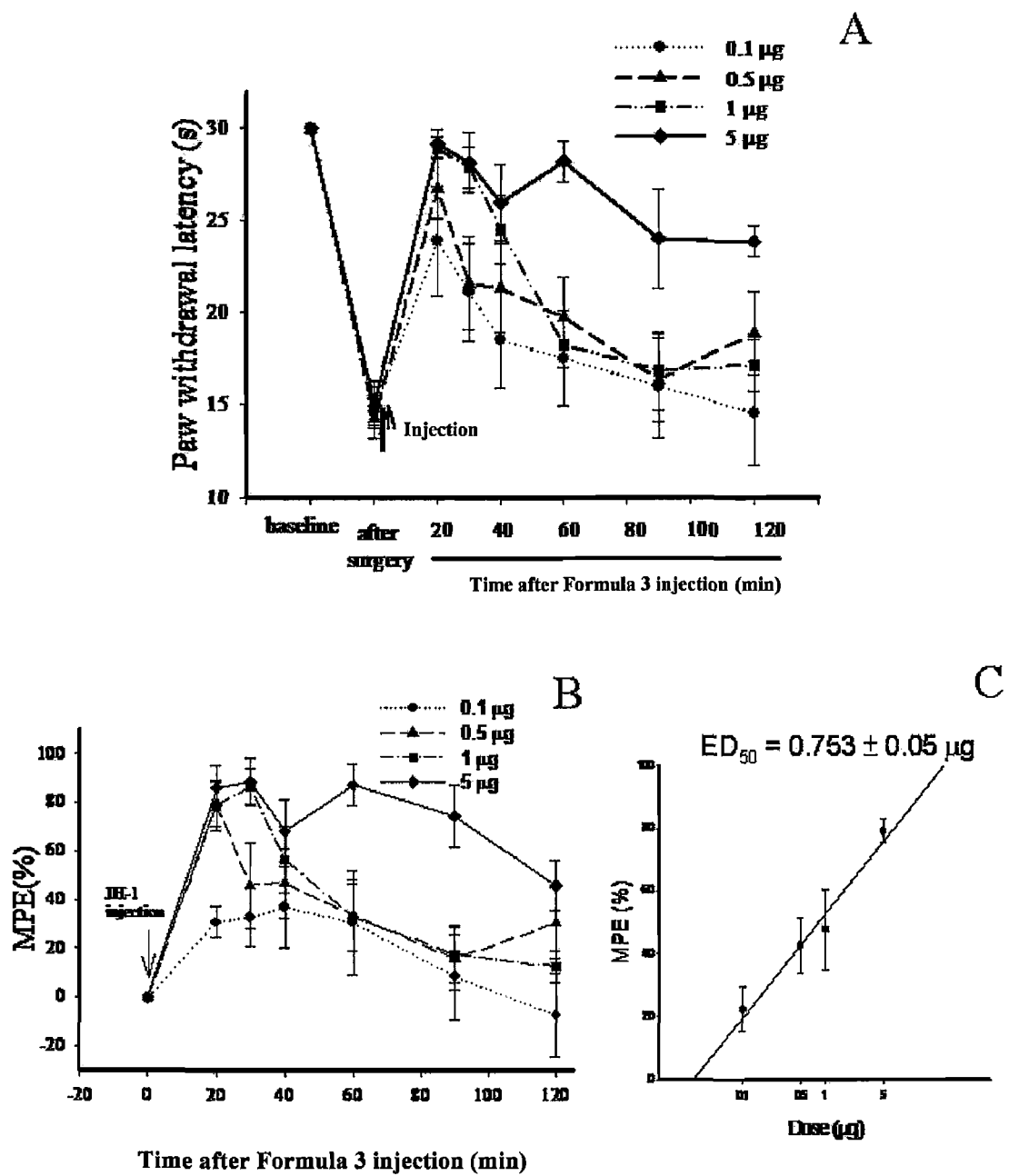
FIG. 2 shows the effect of the compound represented by formula 3 on neuropathic pain relief of chronic constriction injury in the sciatic nerve. A: results of the effect of the compound represented by formula 3 administered intrathecally at different concentrations on paw withdrawal latency; B: maximum percent effect (MPE) of the compound represented by formula 3 administered intrathecally; C: the dose-response curve and 50% effective dose ($ED_{50}$) of the compound represented by formula 3 calculated with MPE. Each point was repeated at least six times.

The results of neuropathic pain relief are shown in FIG. 2. Thermal hyperalgesia started on day 7 after sciatic nerve injury. The paw withdrawal latency decreased from 30 seconds to about 14 seconds. Intrathecal injections of the compound represented by formula 3 of 0.1, 0.5, 1, or 5 μg all show significant effect on thermal hyperalgesia inhibition. After calculating the MPE, the 50% effective dose ($ED_{50}$) is 0.75±0.05 μg.

Atherosclerosis Model in Rat

The operation was performed according to the references of Berger et al (Atherosclerosis 175:229-234, 2004) and Chen et al (Naunyn Schmiedebergs Arch Pharmacol 368:127-133, 2003). The animals were anesthetized with 2.5% isoflurane (mixed air and oxygen of 1:1) with a 2F probe balloon catheter. The catheter was pre-filled with saline solution and positioned from the external carotid artery of the right neck into the right common carotid artery. When the catheter entered about 1.5 cm of the right common carotid artery, the balloon was inflated and rubbed forward and backward three times. Then, the catheter was removed and the external carotid artery was ligated and the incision was sutured. The animals were sacrificed after three weeks and the common carotid artery from both sides were taken and fixed with 4% paraformaldehyde for one day and sliced (3 μm) and subjected to H & E stain. The samples were observed under an optical microscope and photoed. The thickness of neointimal proliferation was determined. The right side of each rat was taken as the experiment group and the left side was as the control group.

In the experiment group, the compound represented by formula 3 was administered. The preliminary result shows that neointimal proliferation is significantly improved by administering the compound once a day.

Figure 3:
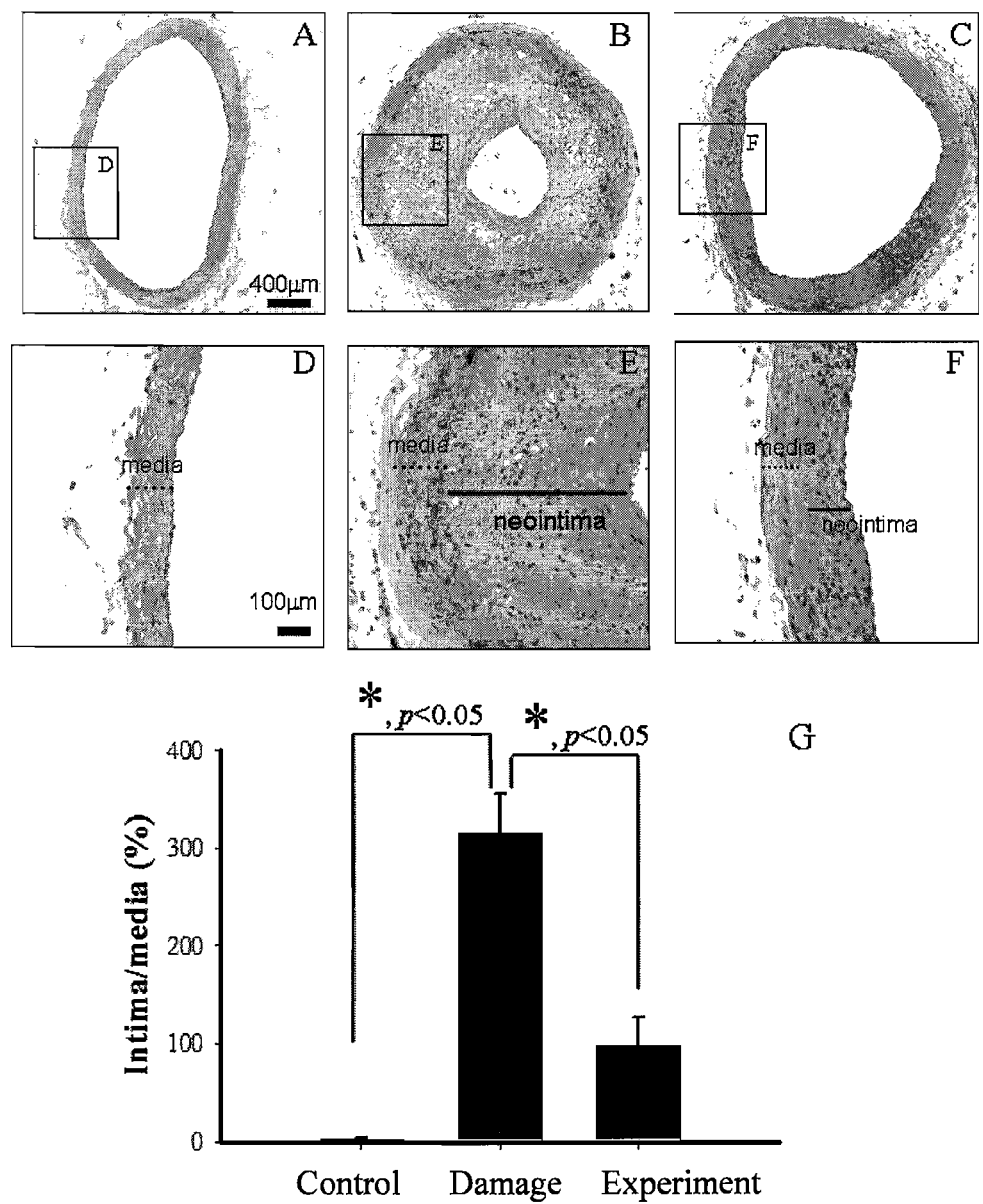
FIG. 3 shows the effect of the compound represented by formula 3 on neointimal proliferation of the carotid artery stimulated by balloon-induced angioplasty. A: control group; B: damage group; C: experiment group treated with the compound represented by formula 3; D, E, and F are the enlarged view of A, B, and C, respectively; G: statistical results of numeralizing the intima/media.

The effect of anti-atherosclerosis on the atherosclerosis stimulated by balloon-induced angioplasty is shown in FIG. 3. On day 24 after operation, neointimal proliferation in carotid artery was observed in the slice. The compound represented by formula 3 was administered from day 10 to 24 after operation through hypodermic injection with 3 mg/kg a day, and it improves the neointimal proliferation stimulated by balloon-induced angioplasty. When numeralizing the intima/media, it is found that the compound represented by formula 3 improves atherosclerosis significantly.

Multiple Sclerosis Animal Model

Female Lewis rats weighted between 280 to 300 g were used in the multiple sclerosis (MS, also called Encephalomyelitis; EAE) model (Boulerne et al, J Neurosci. 2002; 22:123-32, 2004). The animals were anesthetized with 2.5% isoflurane, and 50 μL of Complete Freund's Adjuvant (Sigma) containing 1 mg inactivated *Mycobacterium tuberculosis* H37Ra and 50 μg guinea pig myelin basic protein (MBP) was subcutaneous injected from the posterior paw for 100% immunizing. In the control group, the rats were injected with Freund's complete adjuvant containing inactivated *Mycobacterium tuberculosis* H37Ra and without guinea pig myelin basic protein. The ill was observed on day 11 to 12 after immunization, and reached the peak on day 14 to 15.

The neural function was assessed on day 15. The scores represents: 0: no clinical symptom; 1: function loss in the tail; 2: partial paralysis in the posterior limbs; 3: complete paralysis in the posterior limbs; 4: paralysis in the four limbs; 5: complete paralysis in the whole body; 6: death (Liu et al. J Neuroimmunol. 2003; 139:27-35, 1998).

The rats were divided into four groups, and each group containing four animals:

Control group: Rats were subcutaneous injected from the posterior paw with Freund's complete adjuvant containing inactivated *Mycobacterium tuberculosis* H37Ra and without guinea pig myelin basic protein. 20 μL of normal saline was administered through the intrathecal catheter twice a day for five days from day 7.

Multiple sclerosis group: Rats were subcutaneous injected from the posterior paw with Freund's complete adjuvant containing inactivated *Mycobacterium tuberculosis* H37Ra and guinea pig myelin basic protein. 20 μL of normal saline was administered through the intrathecal catheter twice a day for five days from day 7.

Multiple sclerosis with treatment group: Rats were subcutaneous injected from the posterior paw with Freund's complete adjuvant containing inactivated *Mycobacterium tuberculosis* H37Ra and guinea pig myelin basic protein. 10 μg/20 μL of compound represented by formula 3 was administered through the intrathecal catheter twice a day for five days from day 7.

Normal rats with treatment group: 10 μg/20 μL of compound represented by formula 3 was administered through the intrathecal catheter twice a day for five days from day 7.

Figure 4:
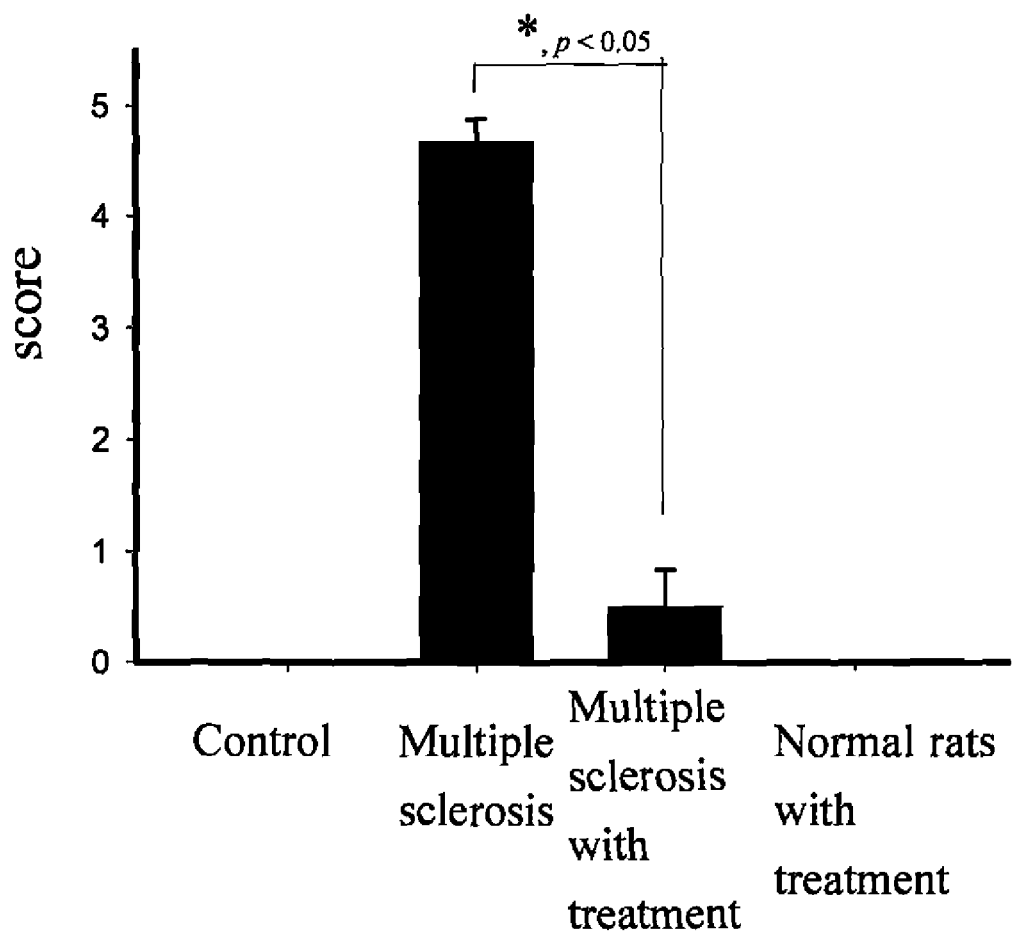
FIG. 4 shows the effect of the compound represented by formula 3 on multiple sclerosis.
Figure 5A:
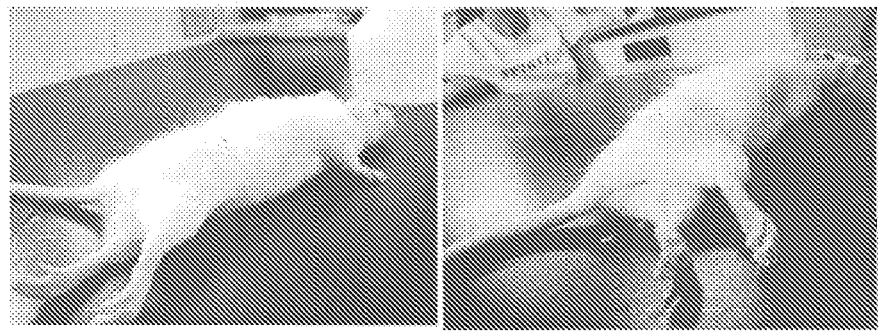
FIG. 5 shows the photographs of multiple sclerosis animal models without treatment (a) and treated with the compound represented by formula 3 (b).
Figure 5B:
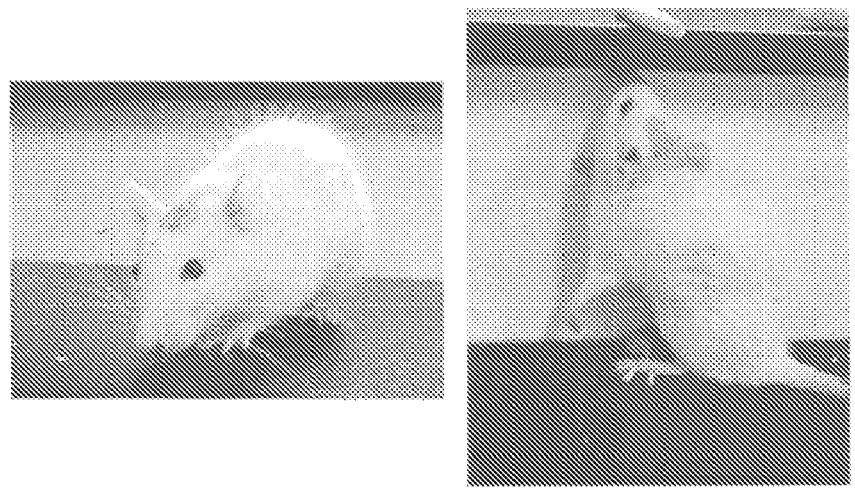

The scores of the control group and normal rats with treatment group are 0. The score of multiple sclerosis group is 4.6±0.2 and that of the multiple sclerosis with treatment group is 0.5±0.3. It shows that administering the compound represented by formula 3 through the intrathecal catheter significantly represses the progress of multiple sclerosis (FIGS. 4 and 5).

Statistics

All data were exhibited with average±standard deviation S.E.M. and analyzed with one-way analysis of variance (ANOVA) and Dunnett's test. P<0.05 shows significant difference. In the anti-inflammation assay in vitro, administering only LPS was taken as 100%. In the animal model, each group was repeated four to eight times.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A compound represented by the following general formula 1,

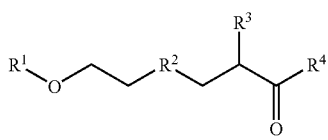

formula 1 wherein:
$R^1$ is selected from the group consisting of H, $R^5$ and $R^5C(=O)$;
$R^2$ is selected from the group consisting of S and $(O=)S(=O)$;
$R^3$ is selected from the group consisting of H, $CH_3$ and $CH_2CH_2C(=O)OR^5$;
$R^4$ is selected from the group consisting of $R^5$, $OR^5$,

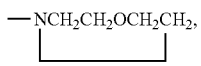

$N(R^5)_2$, $NH_2$, $NHR^5$ and OH; and
$R^5$ is selected from an alkyl group having one to six carbon atoms and a phenyl group;
provided that when $R^3$ is $CH_2CH_2C(=O)OR^5$, $R^4$ is $OR^5$; and
when $R^1$ is H, $R^2$ is S and $R^3$ is H, $R^4$ is not $CH_3$;
wherein the compound is selected from the group consisting of the compounds represented by the following formulae 3, 4, 5, 7, 9, 11, 12, 13, 16, 17, 18, 19, 21 and 22,

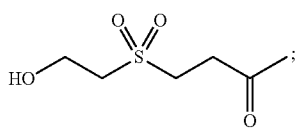

formula 3

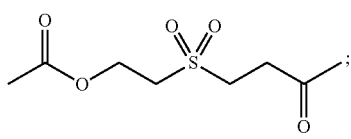

formula 4

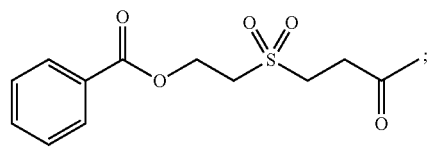

formula 5

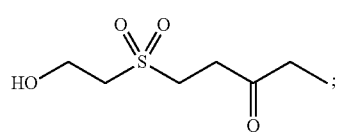

formula 7

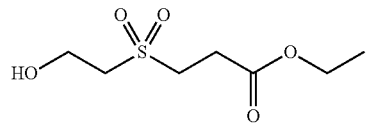

formula 9

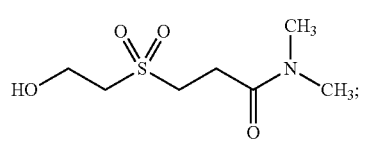

formula 11

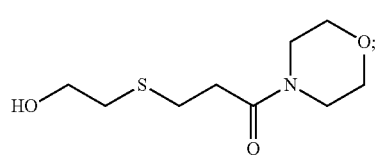

formula 12

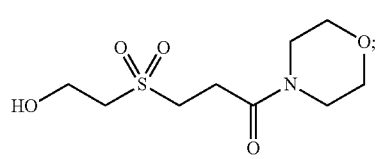

formula 13

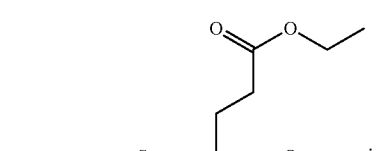

formula 16

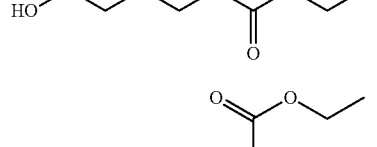

formula 17

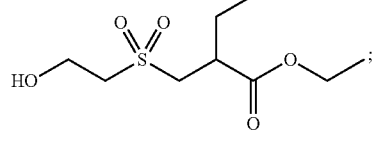

formula 18

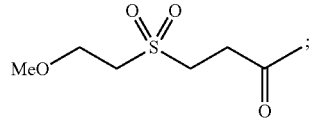

formula 19

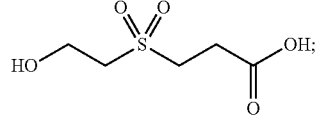

formula 21

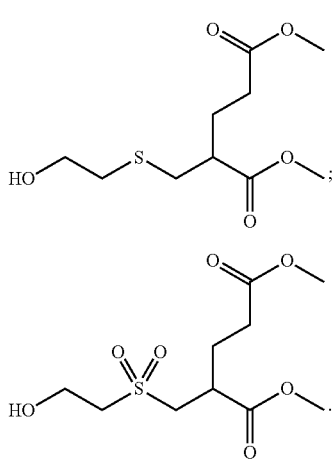

formula 22

2. A compound represented by the following general formula 2, formula 2

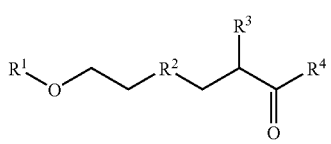

wherein:
R¹ is selected from the group consisting of H, R⁵ and R⁵C(=O);
R² is selected from the group consisting of S and (O=)S(=O);
R³ is selected from the group consisting of H, CH₃ and CH₂CH₂C(=O)OR⁵;
R⁴ is selected from the group consisting of R⁵, OR⁵,

N(R⁵)₂, NH₂, NHR⁵ and OH; and
R⁵ is selected from an alkyl group having one to six carbon atoms and a phenyl group;
provided that when R³ is CH₂CH₂C(=O)OR⁵, R⁴ is OR⁵;
wherein the compound is selected from the group consisting of the compounds represented by the following formulae 3, 4, 5, 7, 9, 11, 12, 13, 16, 17, 18, 19, 21 and 22, formula 3

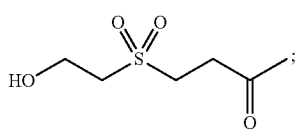

formula 4

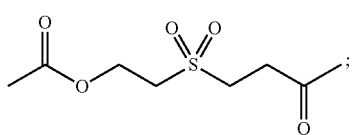

formula 5

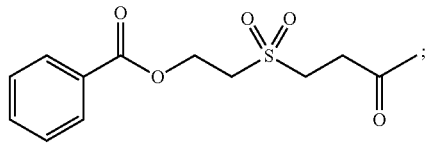

formula 7

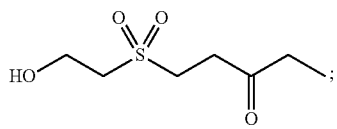

formula 9

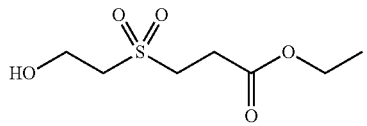

formula 11

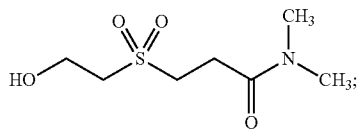

formula 12

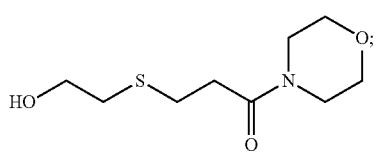

formula 13

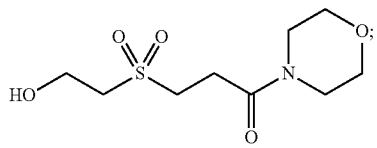

formula 16

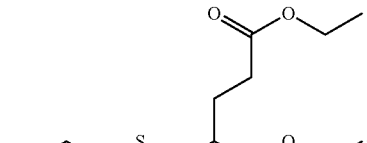

formula 17

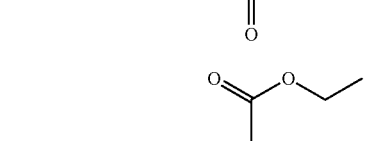

formula 18

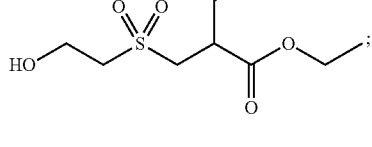

formula 19

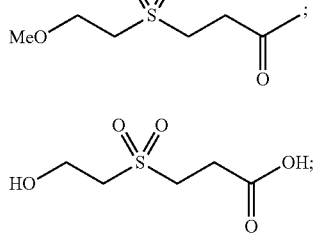

-continued

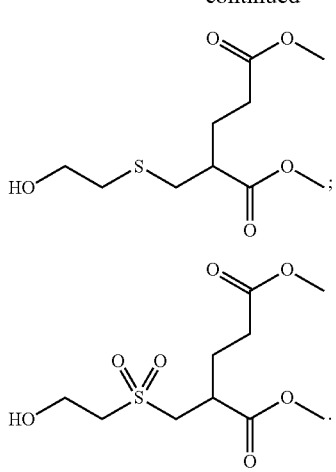

formula 21 formula 22 wherein the compound is synthesized by a method selected from the group consisting of method (I), (IV), (V), and (VI), method (I) when $R^1$ is H and $R^2$ is S, reacting a compound represented by the following general formula 23,

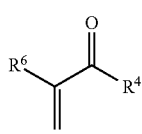

formula 23 with 2-mercaptoethanol represented by the following general formula 24,

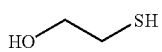

formula 24 to obtain a compound represented by the following general formula 25,

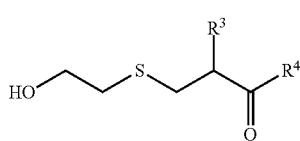

formula 25 for the preparation of formula 12, 16 or 21;

method (IV) when $R^2$ is (O=)S(=O), reacting a compound represented by the general formula 23 with 2-mercaptoethanol to obtain a compound represented by the general formula 25, and oxidizing the compound represented by the general formula 25 for the preparation of formula 3, 7, 9, 11, 13, 17, 19, or 22;

method (V) when $R^1$ is $R^5C(=O)$ and $R^2$ is (O=)S(=O), reacting a compound represented by the general formula 23 with 2-mercaptoethanol to obtain a compound represented by the general formula 25, and esterifying and oxidizing the compound represented by the general formula 25 for the preparation of formula 4 or 5; and method (VI) when $R^1$ is $R^5$ and $R^2$ is (O=)S(=O), reacting a compound represented by the general formula 23 with 2-mercaptoethanol to obtain a compound represented by the general formula 25, and alkylating and oxidizing the compound represented by the general formula 25 for the preparation of formula 18.

3. The compound according to claim 2, wherein $R^3$ is H.

4. The compound according to claim 2, wherein the compounds represented by formulae 23 and 24 are reacted in the presence of triethylamine.

5. The compound according to claim 2, wherein the compounds represented by formulae 23 and 24 are dissolved in acetone.

6. The compound according to claim 2, wherein when $R^3$ is $CH_2CH_2C(=O)OR^5$, the compounds represented by formulae 23 and 24 are reacted in the absence of a solvent.

7. The compound according to claim 2, wherein the esterification is carried out in the presence of triethylamine.

8. The compound according to claim 2, wherein reactants of the esterification are dissolved in dichloromethane.

9. The compound according to claim 2, wherein when $R^1$ is $CH_3C(=O)$, the esterification comprises reacting the compound represented by general formula 25 with acetic anhydride.

10. The compound according to claim 2, wherein when $R^1$ is $C_6H_5C(=O)$, the esterification comprises reacting the compound represented by general formula 25 with benzoyl chloride.

11. The compound according to claim 2, wherein when $R^1$ is $CH_3$, the alkylation comprises reacting the compound represented by general formula 25 with $CH_3I$.

12. The compound according to claim 2, wherein the oxidation is carried out with hydrogen peroxide.

13. The compound according to claim 12, wherein the oxidation is catalyzed by $MnSO_4 \cdot H_2O$.

14. The compound according to claim 12, wherein reactants of the oxidation are dissolved in acetonitrile.

15. The compound according to claim 2, wherein the oxidation is carried out with m-chloroperoxybenzoic acid.

16. The compound according to claim 15, wherein reactants of the oxidation are dissolved in dichloromethane.

* * * * *